United States Patent
Lin et al.

(10) Patent No.: US 11,376,117 B2
(45) Date of Patent: Jul. 5, 2022

(54) 3D PRINTED SPIRAL FOR HYBRID TRACHEAL REPLACEMENT SCAFFOLDS

(71) Applicants: University of Cincinnati, Cincinnati, OH (US); Children's Hospital Medical Center, Cincinnati, OH (US)

(72) Inventors: Chia-Ying James Lin, Mason, OH (US); John van Aalst, Walton, KY (US); Stacey Gruber, Cincinnati, OH (US); Alessandro de Alarcon, Cincinnati, OH (US); Michael A. Helmrath, Cincinnati, OH (US)

(73) Assignees: University of Cincinnati, Cincinnati, OH (US); Children's Hospital Medical Center, Cincinnati, OH (US)

( * ) Notice: Subject to any disclaimer, the term of this patent is extended or adjusted under 35 U.S.C. 154(b) by 214 days.

(21) Appl. No.: 16/643,002

(22) PCT Filed: Aug. 31, 2018

(86) PCT No.: PCT/US2018/049029
§ 371 (c)(1),
(2) Date: Feb. 28, 2020

(87) PCT Pub. No.: WO2019/046684
PCT Pub. Date: Mar. 7, 2019

(65) Prior Publication Data
US 2020/0253727 A1    Aug. 13, 2020

Related U.S. Application Data

(60) Provisional application No. 62/552,688, filed on Aug. 31, 2017.

(51) Int. Cl.
| | |
|---|---|
| A61F 2/20 | (2006.01) |
| A61L 27/18 | (2006.01) |
| A61L 27/36 | (2006.01) |
| A61L 27/38 | (2006.01) |
| A61L 27/56 | (2006.01) |
| B33Y 80/00 | (2015.01) |

(52) U.S. Cl.
CPC ............. *A61F 2/20* (2013.01); *A61L 27/18* (2013.01); *A61L 27/3633* (2013.01);
(Continued)

(58) Field of Classification Search
CPC .............. A61L 27/00–60; A61F 2/20; A61F 2210/0004; A61F 2220/0075;
(Continued)

(56) References Cited

U.S. PATENT DOCUMENTS

2014/0072610 A1   3/2014   Venkatraman et al.
2015/0094808 A1   4/2015   Macchiarini

OTHER PUBLICATIONS

Kojima, K, et al. (2003) A composite tissue-engineered trachea using sheep nasal chondrocyte and epithelial cells The FASEB Journal 17(8):823-8 (Year: 2003).*

(Continued)

*Primary Examiner* — Brian A Dukert
*Assistant Examiner* — Rebecca Lynee Zimmerman
(74) *Attorney, Agent, or Firm* — Dinsmore & Shohl LLP (57) ABSTRACT

Various aspects of the disclosure relate to a tracheal implant comprising (a) a trachea processed to comprise one or more incisions providing a helical configuration to the processed trachea; and (b) a subject-specific synthetic support.

23 Claims, 5 Drawing Sheets

(52) U.S. Cl.
CPC ....... *A61L 27/3683* (2013.01); *A61L 27/3834* (2013.01); *A61L 27/56* (2013.01); *A61F 2210/0004* (2013.01); *A61F 2220/0075* (2013.01); *A61F 2230/0091* (2013.01); *A61F 2250/0067* (2013.01); *B33Y 80/00* (2014.12)

(58) Field of Classification Search
CPC ...... A61F 2230/0091; A61F 2250/0067; A61F 2220/005; B33Y 80/00
See application file for complete search history.

(56) References Cited

OTHER PUBLICATIONS

George Z. Cheng et al., 3D Printing and Personalized Airway Stents; Pulm Ther, Jan. 6, 2017.
Johannes C. Haag et al., Tracheal Replacement for Primary Tracheal Cancer, Curr Opin Otolaryngol Head Neck Surg 21:171-177, Apr. 2013.
Siba Haykal et al., Advances in Tracheal Reconstruction, www.prsgo.com, Jul. 2014, pp. 1-11.
Koji Kojima and Charles A. Vacanti, Tissue Engineering in the Trachea, The Anatomical Record, 297:44-50, 2014.
Brooks Udelsman et al., A Reassessment of Tracheal Substitutes—A Systematic Review, Ann Cardiothorac Surg 7(2):175-182, 2018.
International Search Report and Written Opinion for corresponding PCT/US2018/049029 dated Jan. 3, 2019.

* cited by examiner

3D PRINTED SPIRAL FOR HYBRID TRACHEAL REPLACEMENT SCAFFOLDS

CROSS-REFERENCE TO RELATED APPLICATIONS

This patent application is a § 371 U.S. National Stage Application of International Application No. PCT/US2018/049029, filed Aug. 31, 2018, and claims priority to U.S. Provisional Patent Application No. 62/552,688, filed Aug. 31, 2017, each of which is hereby incorporated by reference in its entirety.

GOVERNMENT SUPPORT

This invention was made with government support under Grant R21EB025378-01 awarded by the United States National Institute of Biomedical Imaging and Bioengineering. The government has certain rights in the invention.

BACKGROUND

Obstruction of the tracheal airway causes significant morbidity and mortality. Surgical interventions to repair diseased or damaged tracheas typically involve resecting and reconstructing the trachea. Surgical repair is unavailable to all patients, however, because certain lesions cannot be repaired with a high probability of success. The length of tracheal damage is informative. Adults can generally tolerate tracheal resection of up to one-half of the trachea, depending on any confounding factors. Small children can generally tolerate tracheal resection of up to one-third of the trachea. Complete tracheal replacement is therefore the only viable option for patients presenting with extensive damage.

Trachea transplantations are possible in a subset of patients, but transplantation is challenging because transplantation requires the successful restoration of a blood supply to the graft and the administration of immunosuppressants, which impair the ability of a patient to clear infections in the graft.

Tissue engineering presents a promising strategy to meet the demand for implantable tracheas. Thus far, however, de novo designed tracheas have been unsuccessful, for example, because of (1) size and shape limitations of a single scaffold; (2) incomplete endoluminal healing and epithelialization, which result in perforations and infection; (3) lack of glandular function; (4) limited vascularity; (5) inadequate approximation of native mechanical properties; and (6) inability to grow with the patient.

Improved methods of engineering tracheas for implantation are therefore desirable.

SUMMARY

Embodiments of the invention provide a tracheal implant that displays improved performance upon transplantation into a subject. The inventors found that a donor trachea can be surgically processed ex vivo to alter is configuration thereby resulting in a processed donor trachea that is more compatible with a recipient than the unmodified donor trachea. The processed trachea is typically associated with a synthetic support, e.g., to preserve the structural integrity of the processed configuration.

One embodiment is directed to a tracheal implant, comprising (a) a trachea processed to comprise one or more incisions providing a helical configuration to the processed trachea; and (b) a subject-specific synthetic support.

Another embodiment is directed to a method of treating a subject in need of a tracheal implant, comprising: obtaining conformational information of a trachea and implant region of the subject; fabricating a subject-specific synthetic support based on the conformational information; providing a donor trachea; making one or more incisions in the donor trachea to yield a processed trachea; suturing the processed trachea to the synthetic support; and implanting the processed trachea and synthetic support in the subject.

These and other aspects and embodiments will be detailed and clarified by reference to the Drawings and Detailed Description, below.

BRIEF DESCRIPTION OF THE DRAWINGS

Figures have been provided to illustrate specific embodiments, aspects, and features of the invention and should not be construed as limiting the full scope thereof as defined by the appended claims.

FIG. 5 contains five panels labeled panels A, B, C, D, and E. Each panel is an image of the same tracheal implant obtained by bronchoscopy one month after implantation of the tracheal implant into a rabbit. Panel A shows an image of the vocal cords of the trachea. Panel B shows native trachea. Panels C and D show processed trachea and suture lines; the suture lines display minimal scarring. Panel D shows decellularized trachea below the suture lines. The rightward-pointing arrows in panels C and D denote processed trachea that was decellularized in the tracheal implant and now displays cellular tissue. The downward-pointing arrows in panels C and D denote the suture lines. (a) denotes the anterior region of the trachea; (p) denotes the posterior region of the trachea; (s) denotes the superior region of the trachea; and (i) denotes the inferior region of the trachea.

DETAILED DESCRIPTION

Humans have tracheas of different shapes and sizes, which often confounds tracheal allografts. A successful trachea transplant requires native-like re-vascularization and dynamic movement of the graft. Variation between the host and graft is therefore limiting. Pediatric patients display further challenges because suitably-sized tracheas are further limiting and because the graft must grow with the patient.

The inventors discovered an elegant solution to address the shape and size limitations of tracheal transplantation. A tracheal graft may be cut into a helix, and the helix may be overwound or underwound to decrease or increase its diameter, respectively, and/or increase or decrease its length, respectively. The tracheal graft can also be fixed to a synthetic support to preserve the structural integrity of the overwound or underwound configuration in situ.

The inventors contemplate that alternate configurations may allow the surgical adjustment of a donor trachea to fit a host. A longitudinal strip of donor trachea could be removed, for example, to decrease the diameter of a donor trachea. A helix nevertheless presents unique advantages, for example, because the defect introduced by surgically altering a donor trachea is evenly distributed in three dimensions when an incision is a helical incision.

Some embodiments relate to a tracheal implant. In specific embodiments, the tracheal implant comprises a trachea processed to comprise one or more incisions providing a helical configuration to the processed trachea. In specific embodiments, the tracheal implant comprises a subject-specific synthetic support.

In specific embodiments, the processed trachea comprises a lumen comprising a diameter, wherein the diameter varies from a diameter prior to processing. In more specific embodiments, the diameter varies from the diameter prior to processing by 200 μm to 2 cm.

In specific embodiments, the tracheal implant comprises a processed trachea, or a portion thereof, and a synthetic support associated with the processed trachea.

In specific embodiments, the tracheal implant comprises a processed trachea comprising one or more incisions and configured in a processed configuration; and a synthetic support associated with the processed trachea. In specific embodiments, the processed configuration requires the one or more incisions. In more specific embodiments, the one or more incisions define a helix.

The term "subject-specific" as utilized herein means that a synthetic support is shaped and sized for transplantation into a specific subject.

The concave, luminal surface of a synthetic support is typically shaped to fit a convex surface at or near the perichondrium of the processed trachea. The existing trachea of the subject as imaged by computed tomography or magnetic resonance imaging may be informative. Lesions and inflammation may limit the ability to prepare an ideal model, but an informed model is nevertheless superior to guesswork.

In specific embodiments, a processed trachea is obtained from an unprocessed, donor trachea. The shape and/or size of the unprocessed trachea typically vary from the shape and/or size of the synthetic support. The variation in shape and/or size of the unprocessed trachea from an ideal fit favors the use of a tracheal implant disclosed herein rather than the unprocessed trachea.

In specific embodiments, a processed trachea comprises a single, continuous tissue. In specific embodiments, a processed trachea comprises decellularized tissue.

In specific embodiments, an unprocessed trachea or a processed trachea is decellularized, i.e., the trachea is substantially free of cells of the trachea donor. In specific embodiments, an unprocessed trachea or processed trachea nevertheless comprises cells such as stem cells, adipocytes, and tracheal cells (e.g., goblet cells), which may be added to a tracheal implant to increase its rate of recellularization and incorporation into a subject.

In specific embodiments, a processed trachea comprises stem cells, adipocytes, and/or tracheal cells (e.g., goblet cells) in its lumen. In more specific embodiments, the origin of the stem cells, adipocytes, and/or tracheal cells is a different individual than the origin of the processed trachea. In very specific embodiments, the different individual is the intended recipient of the tracheal implant (i.e., a subject as described herein).

In specific embodiments, a processed trachea is a human trachea.

In specific embodiments, a processed trachea comprises one or more incisions such that the shape and size of the processed trachea is compatible with the synthetic support. In more specific embodiments, a processed trachea is more compatible with a synthetic support than an unprocessed trachea lacking the one or more incisions, e.g., such as the unprocessed trachea from which the processed trachea originated.

In specific embodiments, a processed trachea exists in a processed configuration within a tracheal implant. The one or more incisions allow the processed trachea to be configured in the processed configuration. In specific embodiments, a processed trachea also has a native configuration. The native configuration corresponds to the configuration of the trachea prior to processing, and the native configuration is therefore independent of the one or more incisions.

In specific embodiments, a processed configuration and the native configuration each define a different lumen, wherein each lumen is empty space encircled by the processed trachea. Each lumen has a diameter by definition. In specific embodiments, the diameter of the lumen of a processed configuration is different from the diameter of the lumen of a native configuration.

In specific embodiments, a processed configuration and a native configuration of a processed trachea are different, mutually exclusive geometries of the trachea. In very specific embodiments, a tracheal implant described herein comprises a processed trachea comprising a processed configuration. In very specific embodiments, a native configuration is relevant to describe the processed configuration.

In specific embodiments, a processed trachea is a helix defined by the one or more incisions. The one or more incisions can define a helix. In some embodiments, an incision is made by rotating and translating a donor trachea about its axis relative to a blade; rotating and translating a blade relative to the axis of the trachea; rotating the blade and translating the trachea; or rotating the trachea and translating the blade. Such an incision converts an unprocessed, donor trachea, which is a three-dimensional tube, into a processed trachea that is a coiled, approximate two-dimensional quadrilateral (i.e., a helix) or a coiled, approximate irregular hexahedron (i.e., a helix). In specific embodiments, the coil of the helix of the processed trachea is then be overwound or underwound into a processed configuration, e.g., to fit a synthetic support.

In specific embodiments, a processed configuration and a native configuration each have a helix that is defined by the one or more incisions. In specific embodiments, the helix of the processed configuration is overwound or underwound relative to the native configuration. In more specific embodiments, the processed configuration defines a lumen comprising a diameter, and the diameter is different from the diameter of a lumen defined by the native configuration. In even more specific embodiments, the diameter of the lumen of a processed trachea is about 200 μm to about 2 cm in the processed configuration.

The term "overwound" as utilized herein means that a processed configuration encircles its axis more than the native configuration. For example, an incision in a processed configuration may encircle the axis of a trachea at least 1.01 times more than the same incision in a native configuration. An overwound, processed configuration has a greater angle, longer length, smaller diameter, and smaller circumference than the native configuration.

The term "underwound" as utilized herein means that a processed configuration encircles its axis less than the native configuration. For example, an incision in a processed configuration may encircle the axis of a trachea less than 0.99 times than the same incision in a native configuration. An underwound, processed configuration has a smaller angle, shorter length, greater diameter, and greater circumference than the native configuration.

In some embodiments, the processed configuration of a processed trachea is overwound or underwound relative to the native configuration of the processed trachea thereby resulting in a smaller lumen or larger lumen than the native configuration, respectively.

A trachea, also known as the windpipe, connects the pharynx and larynx to the lungs, thereby allowing air to pass from the nose and/or mouth into the lungs. The trachea is a tube that is approximately cylindrical in shape. A trachea has an axis, which is the axis of the approximate cylindrical shape. A trachea comprises an anterior, head-facing end and an opposite, posterior, lung-facing end, which correspond to alternate ends of the approximate cylindrical shape.

In some embodiments, a trachea either comprises one or more incisions that define a helix or the trachea exists in a helical configuration. In some embodiments, a processed configuration is a helical configuration. In some embodiments, a native configuration is a helical configuration, e.g., when a trachea having a native configuration has one or more incisions that define a helix.

A helix can be defined by (a) identifying a line perpendicular to the axis of the trachea and intersecting both the axis and the trachea; (b) rotating the line about the axis at a constant rate while maintaining the perpendicular angle and intersection with the axis; and (c) simultaneously translating the line along the axis at a constant rate while maintaining the perpendicular angle and intersection with the axis. The line may define an incision. The incision typically defines different, related helices in the processed configuration and in the native configuration.

A helix comprises a lead. The term "lead" as utilized herein refers to the length of a line segment in Cartesian space between two points on a helix that are related by a 360° rotation of the helix about its axis. The line segment is in plane with the axis in Cartesian space by definition. When the helix has a regular, cylindrical shape (i.e., the helix is a general helix or a cylindrical helix), then the line segment is parallel to the axis in Cartesian space.

An incision that defines one or more helices typically creates an anterior surface and a posterior surface. The anterior surface faces the anterior end of the trachea as the term "anterior surface" is utilized herein. The posterior surface faces the posterior end of the trachea as the term "posterior surface" is utilized herein. The phrase "related by a 360° rotation of the helix about its axis" can refer to two points that both occur on the anterior surface or that both occur the posterior surface, but the phrase does not refer to a point that occurs on the anterior surface and a point that does not occur on the anterior surface, the phrase does not refer to a point that occurs on the posterior surface and a point that does not occur on the posterior surface, and the phrase should be interpreted according to the foregoing concepts. Should the conceptual interpretation be found ambiguous, then the lead is the average length of the line segments, in Cartesian space, between two consecutive points on the anterior surface of a helix that are related by a 360° rotation of the anterior surface about the axis of the trachea.

A helix comprises an angle. The angle of the helix may be identified many different ways. The angle is, for example, the arctangent of the lead divided by the circumference of the trachea. The skilled person will immediately recognize that the angle varies with circumference. The term "angle" as utilized herein to describe a helix corresponds to the average circumference of a trachea taken at the middle of the tracheal tissue between the perichondrium and epithelial surfaces of the trachea.

A helix comprises a pitch. In some embodiments, the pitch is equal to the lead. In some embodiments, the pitch is a multiple of the lead, for example, if the processed trachea comprises multiple pieces of intertwined tracheal tissue. In specific embodiments, a processed trachea is configured by making two incisions that result in a double helix comprising two pieces of intertwined tracheal tissue.

A helix comprises a diameter. The diameters described herein refer to the average diameter of a trachea taken at the middle of the tracheal tissue between the perichondrium and epithelial surfaces of the trachea unless otherwise indicated by context.

In some embodiments, an incision is made in an unprocessed, donor trachea at an angle of about 5° to about 85° relative to the axis of the unprocessed, donor trachea such as about 5° to about 25°, about 15° to about 35°, about 25° to about 45°, about 35° to about 55°, about 45° to about 65°, about 55° to about 75°, about 65° to about 85°, about 5° to about 15°, about 10° to about 20°, about 15° to about 25°, about 20° to about 30°, about 25° to about 35°, about 30° to about 40°, about 35° to about 45°, about 40° to about 50°, about 45° to about 55°, about 50° to about 60°, about 55° to about 65°, about 60° to about 70°, about 65° to about 75°, about 70° to about 80°, or about 75° to about 85°. This angle defines a helix relative to the unprocessed, donor trachea. In specific embodiments, the angle of the helix relative to an unprocessed, donor trachea is the angle of the helix of a native configuration of a processed trachea.

The angle of the incision and diameter of the unprocessed, donor trachea defines the lead of the helix. In some embodiments, an incision is made in an unprocessed, donor trachea having a lead of about 1 mm to about 8 cm such as about 1 mm to about 2 cm, about 1 cm to about 3 cm, about 2 cm to about 4 cm, about 3 cm to about 5 cm, about 4 cm to about 6 cm, about 5 cm to about 7 cm, about 6 cm to about 8 cm, about 1 mm to about 10 mm, about 5 mm to about 15 mm, about 10 mm to about 20 mm, about 15 mm to about 25 mm, about 20 mm to about 30 mm, about 25 mm to about 35 mm, about 30 mm to about 40 mm, about 35 mm to about 45 mm, about 40 mm to about 50 mm, about 45 mm to about 55 mm, about 50 mm to about 60 mm, about 55 mm to about 65 mm, about 60 mm to about 70 mm, about 65 mm to about 75 mm, or about 70 mm to about 80 mm. In specific embodiments, the lead of the helix relative to an unprocessed, donor trachea is the lead of the helix of a native configuration of a processed trachea.

In specific embodiments, the lead of a helix is the same size as the pitch of a helix. In specific embodiments, the lead of the helix is 2 times, 3 times, or 4 times the size of the pitch of a helix.

The diameter of the lumen of an adult human trachea is about 15 mm to about 20 mm. The diameter of the lumen of a pediatric human trachea can range from about 4 mm to about 20 mm. In specific embodiments, the diameter of the lumen of an unprocessed trachea is therefore about 4 mm to about 20 mm, such as about 4 mm to about 15 mm, about 4 mm to about 12 mm, or about 15 mm to about 20 mm. In specific embodiments, the diameter of the lumen of the native configuration of a processed trachea is about 4 mm to about 20 mm, such as about 4 mm to about 15 mm, about 4 mm to about 12 mm, or about 15 mm to about 20 mm.

In specific embodiments, a processed trachea is over-wound or underwound relative to the native configuration of the processed trachea. The over-winding or under-winding of the processed trachea alters the angle of the helix of the processed trachea relative to the angle of the incision made in the unprocessed trachea. In specific embodiments, the over-winding or under-winding of the processed trachea alters the angle of the helix of the processed configuration relative to the native configuration of the trachea. The angle of the helix of a processed configuration is referred to herein as a "first angle," and the angle of the helix of a native configuration is referred to herein as a "second angle."

In specific embodiments, the angle of a helix of a processed configuration is about 5° to about 85° relative to the axis of the processed trachea such as about 5° to about 25°, about 15° to about 35°, about 25° to about 45°, about 35° to about 55°, about 45° to about 65°, about 55° to about 75°, about 65° to about 85°, about 5° to about 15°, about 10° to about 20°, about 15° to about 25°, about 20° to about 30°, about 25° to about 35°, about 30° to about 40°, about 35° to about 45°, about 40° to about 50°, about 45° to about 55°, about 50° to about 60°, about 55° to about 65°, about 60° to about 70°, about 65° to about 75°, about 70° to about 80°, or about 75° to about 85°.

In specific embodiments, a first angle and a second angle vary by at least 1°, 2°, 3°, 4°, 5°, 6°, 7°, 8°, 9°, 10°, 11°, 12°, 13°, 14°, 15°, 16°, 17°, 18°, 19°, 20°, 21°, 22°, 23°, 24°, 25°, 26°, 27°, 28°, 29°, 30°, 31°, 32°, 33°, 34°, 35°, 36°, 37°, 38°, 39°, 40°, 41°, 42°, 43°, 44°, 45°, 46°, 47°, 48°, 49°, 50°, 51°, 52°, 53°, 54°, 55°, 56°, 57°, 58°, 59°, 60°, 61°, 62°, 63°, 64°, 65°, 66°, 67°, 68°, 69°, 70°, 71°, 72°, 73°, 74°, 75°, 76°, 77°, 78°, 79°, 80°, 81°, 82°, 83°, 84°, 85°, 86°, 87°, 88°, or 89°. In very specific embodiments, a first angle and second angle vary by 1° to 40°, 10° to 50°, 20° to 60°, 30° to 50°, 40° to 80°, 50° to 89°, 1° to 20°, 10° to 30°, 20° to 40°, 30° to 50°, 40° to 60°, 50° to 70°, 60° to 80°, 70° to 89°, 1° to 10°, 5° to 15°, 10° to 20°, or 15° to 25°.

The over-winding or under-winding of the processed trachea alters the lead of the helix of the processed configuration relative to the lead of the incision made in the unprocessed trachea. The over-winding or under-winding of the processed trachea alters the lead of the helix of the processed configuration relative to the native configuration of the processed trachea. The lead of the helix of a processed configuration is referred to herein as a "first lead," and the lead of the helix of a native configuration is referred to herein as a "second lead."

In specific embodiments, a lead of a helix of a processed configuration is about 1 mm to about 8 cm such as about 1 mm to about 2 cm, about 1 cm to about 3 cm, about 2 cm to about 4 cm, about 3 cm to about 5 cm, about 4 cm to about 6 cm, about 5 cm to about 7 cm, about 6 cm to about 8 cm, about 1 mm to about 10 mm, about 5 mm to about 15 mm, about 10 mm to about 20 mm, about 15 mm to about 25 mm, about 20 mm to about 30 mm, about 25 mm to about 35 mm, about 30 mm to about 40 mm, about 35 mm to about 45 mm, about 40 mm to about 50 mm, about 45 mm to about 55 mm, about 50 mm to about 60 mm, about 55 mm to about 65 mm, about 60 mm to about 70 mm, about 65 mm to about 75 mm, or about 70 mm to about 80 mm.

In specific embodiments, a first lead and a second lead vary by at least 100 µm, 200 µm, 300 µm, 400 µm, 500 µm, 600 µm, 700 µm, 800 µm, 900 µm, 1.0 mm, 1.2 mm, 1.5 mm, 2.0 mm, 2.5 mm, 3 mm, 4 mm, 5 mm, 6 mm, 7 mm, 8 mm, 9 mm, or 10 mm. In very specific embodiments, a first lead and a second lead vary by about 100 µm to about 5 cm such as about 200 µm to about 2 cm or about 500 µm to about 5 mm.

The over-winding or under-winding of the processed trachea alters the pitch of the helix of the processed configuration relative to the pitch of the incision made in the unprocessed trachea. The over-winding or under-winding of the processed trachea alters the pitch of the helix of the processed configuration relative to the native configuration of the processed trachea. The pitch of the helix of a processed configuration is referred to herein as a "first pitch," and the pitch of the helix of a native configuration is referred to herein as a "second pitch."

In specific embodiments, a first pitch and a second pitch vary by at least 100 µm, 200 µm, 300 µm, 400 µm, 500 µm, 600 µm, 700 µm, 800 µm, 900 µm, 1.0 mm, 1.2 mm, 1.5 mm, 2.0 mm, 2.5 mm, 3 mm, 4 mm, 5 mm, 6 mm, 7 mm, 8 mm, 9 mm, or 10 mm. In very specific embodiments, a first pitch and a second pitch vary by about 100 µm to about 5 cm such as about 200 µm to about 2 cm or about 500 µm to about 5 mm.

The over-winding or under-winding of the processed trachea alters the diameter of the lumen of the processed configuration relative to the diameter of the lumen of the native configuration. The diameter of the lumen of a processed configuration is referred to herein as a "first diameter," and the diameter of the lumen of a native configuration is referred to herein as a "second diameter."

In specific embodiments, the diameter of the lumen of a processed configuration is about 4 mm to about 20 mm, such as about 4 mm to about 15 mm, about 4 mm to about 12 mm, or about 15 mm to about 20 mm.

In specific embodiments, a first diameter and a second diameter vary by at least 100 µm, 200 µm, 300 µm, 400 µm, 500 µm, 600 µm, 700 µm, 800 µm, 900 µm, 1.0 mm, 1.2 mm, 1.5 mm, 2.0 mm, 2.5 mm, 3 mm, 4 mm, 5 mm, 6 mm, 7 mm, 8 mm, 9 mm, 10 mm, 15 mm, 20 mm, 25 mm, 3 cm, or 4 cm. In very specific embodiments, a first diameter and a second diameter vary by about 100 µm to about 15 cm such as about 200 µm to about 10 cm or about 500 µm to about 5 cm.

In some embodiments, the length of an overwound processed trachea along its axis is greater than the length of the unprocessed trachea from which the processed trachea originated.

In some embodiments, the processed trachea is a single, continuous tissue. In specific embodiments, a single incision is made in an unprocessed trachea following a helical path in the unprocessed trachea that results in the conversion of a tube-shaped, unprocessed trachea into a helical, processed trachea that is a single, continuous tissue. In some embodiments, one or more additional incision(s) are nevertheless made in an unprocessed trachea, which result in two or more discontinuous tissues. In some embodiments, an incision is made orthogonal to the axis of the unprocessed trachea, for example, to orient the dorsal and ventral faces of an overwound or underwound processed trachea.

In some embodiments, a processed trachea comprises one or more incisions, wherein none of the one or more incisions is linear in Cartesian space. An example of a linear incision is an incision parallel to the axis of the trachea. In some embodiments, a processed trachea comprises one or more incisions, wherein none of the one or more incisions is planar in Cartesian space except for any incisions that define the anterior, head-facing end of the trachea and any incisions that define the posterior, lung-facing end of the trachea, which are typically approximately planar. An example of a planar incision is an incision perpendicular to the axis of the trachea such as certain incision(s) that define the anterior, head-facing end of the trachea and the posterior, lung-facing end of the trachea.

In some embodiments, a processed trachea lacks any incision that occurs in a plane that includes the axis of the processed trachea in Cartesian space. In some embodiments, a processed trachea lacks any incision that occurs in a plane that is perpendicular to the axis of the processed trachea in Cartesian space except for any incisions that define the anterior, head-facing end of the trachea and any incisions that define the posterior, lung-facing end of the trachea. In some embodiments, a processed trachea lacks any incision that occurs in a plane that either includes the axis of the processed trachea in Cartesian space or that is perpendicular to the axis of the processed trachea in Cartesian space except for any incisions that define the anterior, head-facing end of the trachea and any incisions that define the posterior, lung-facing end of the trachea.

In specific embodiments, an unprocessed trachea or processed trachea is of mammalian origin. In even more specific embodiments, an unprocessed trachea or processed trachea is a human trachea.

In specific embodiments, a synthetic support comprises a biocompatible polymer. In specific embodiments, the biocompatible polymer comprises one or more of poly(caprolactone) (PCL), poly(vinyl acetate) (PVAC), ethylene vinyl acetate polymer (EVA), polyvinyl alcohol (PVA), poly(lactic acid) (PLA), poly(glycolic acid) (PGA), poly(lactic-co-glycolic acid) (PLGA), polyalkyl cyanoacrylate, polyurethane, nylons, stereoisomers of the foregoing, and copolymers of two or more of the foregoing. In more specific embodiments, the biocompatible polymer comprises or consists of poly (caprolactone).

In specific embodiments, a synthetic support is porous. In more specific embodiments, a synthetic support comprises a porosity of about 5% to about 90%. In even more specific embodiments, a synthetic support comprises a porosity of about 5% to about 90% such as about 5% to about 60%, about 20% to about 75%, about 35% to about 90%, about 33% to about 67%, or about 35% to about 60%.

In specific embodiments, a synthetic support comprises pores. In specific embodiments, the pores comprise one or more openings on the surface of the synthetic support. In specific embodiments, the openings consist of space on the surface of the synthetic support that allow fluid outside the synthetic support to be in fluid communication with fluid inside the pores within the synthetic support. In more specific embodiments, at least some of the openings are optionally covered by the processed trachea in a tracheal implant.

In some embodiments, each opening has a surface area of about 1000 $\mu m^2$ to about 100 $mm^2$ such as about 2500 $\mu m^2$ to about 25 $mm^2$, about 5000 $\mu m^2$ to about 10 $mm^2$, or about 10,000 $\mu m^2$ to about 1 $mm^2$. In some embodiments, the openings of the pores of a synthetic support have an average surface area of about 1000 $\mu m^2$ to about 100 $mm^2$ per opening such as about 2500 $\mu m^2$ to about 25 $mm^2$, about 5000 $\mu m^2$ to about 10 $mm^2$, or about 10,000 $\mu m^2$ to about 1 $mm^2$.

In some embodiments, the size of the openings permits or inhibits the entry of cells and/or naturally-occurring polymeric matrix biomolecules into the synthetic support.

In some embodiments, a synthetic support comprises a network of pores. The phrase "network of pores" as utilized herein includes pores that are branched and/or pores that define more than 2 openings. In specific embodiments, a network of pores comprises openings on the surface of the synthetic support. In specific embodiments, the openings are in fluid communication with the network of pores.

In some embodiments, openings have an average surface area of about 1000 $\mu m^2$ to about 100 $mm^2$ per opening as described herein, supra. In specific embodiments, greater than 50% of the openings on the surface of the synthetic support are in fluid communication with at least 4 other openings on the surface of the synthetic support such that fluid may enter an opening on the surface of the synthetic support and exit the synthetic support through any one of the at least 4 other openings.

In some embodiments, a synthetic support comprises a network of pores, wherein the pores comprise openings on the surface of the synthetic support, and greater than 10%, 20%, 30%, 40%, 50%, 60%, 70%, or 80% of the openings on the surface of the synthetic support are in fluid communication with at least 2, 3, 4, 5, 6, 7, 8, 9, 10, 12, 14, 16, 18, or 20 other openings on the surface of the synthetic support. The term "fluid communication" as utilized herein in the context of a network of pores means that fluid may enter an opening on the surface of a synthetic support and exit the synthetic support through a different opening on the surface of the synthetic support. A first opening is in fluid communication with a second opening, however, even if fluid cannot practically enter the first opening or exit the second opening, if the fluid cannot both enter the first opening and exit the second opening because the processed trachea or some other non-synthetic support feature of a tracheal implant obscures the first opening and/or the second opening, and the fluid could both enter the first opening and exit the second opening if all such features were removed from the synthetic support.

In very specific embodiments, the openings have an average surface area of about 1000 $\mu m^2$ to about 100 $mm^2$ per opening; and greater than 50% of the openings on the surface of the synthetic support are in fluid communication with at least 4 other openings on the surface of the synthetic support such that fluid may enter an opening on the surface of the synthetic support and exit the synthetic support through any one of the at least 4 other openings.

In some embodiments, a synthetic support comprises a network of pores comprising openings on the surface of the synthetic support and the openings are in fluid communication with the network of pores.

In some embodiments, a synthetic support comprises pores and lacks a network of pores, for example, when each pore is an unbranched void within the synthetic support and each pore comprises 0 to 2 openings. Parallel pores, for example, do not inherently form a network of pores.

In some embodiments, a synthetic support is configured to impart favorable mechanical properties. In some embodiments, a synthetic support comprises a polymer and network of pores that impart favorable mechanical properties.

In specific embodiments, a synthetic support has a compressive modulus of about 1 MPa to about 200 MPa such as about 20 MPa to about 200 MPa. Styrofoam has a compressive modulus of about 1 MPa, for example, and bone has a compressive modulus of about 150 MPa. In very specific embodiments, a synthetic support has a compressive modulus of about 1 MPa to about 70 MPa, about 10 MPa to about 80 MPa, about 20 MPa to about 90 MPa, about 30 MPa to about 100 MPa, about 40 MPa to about 110 MPa, about 50 MPa to about 120 MPa, about 20 MPa to about 70 MPa, about 30 MPa to about 80 MPa, about 40 MPa to about 90 MPa, about 50 MPa to about 100 MPa, about 30 MPa to about 70 MPa, about 40 MPa to about 80 MPa, about 50 MPa to about 90 MPa, about 40 MPa to about 70 MPa, about 50 MPa to about 80 MPa, or 50 MPa to about 70 MPa.

The tensile strength of the synthetic support is not particularly limiting. In specific embodiments, a synthetic support has a tensile strength of about 50 kPa to about 200 MPa such as about 1 MPa to about 10 MPa. In very specific embodiments, a synthetic support has a tensile strength of about 100 kPa to about 150 MPa, about 500 kPa about 100 MPa, or about 800 kPa to about 50 MPa.

The shear stress strength of the synthetic support is not particularly limiting. In specific embodiments, a synthetic support has a shear stress strength of about 50 kPa to about 200 MPa. In very specific embodiments, a synthetic support has a shear stress strength of about 100 kPa to about 150 MPa, about 500 kPa to about 100 MPa, or about 800 kPa to about 50 MPa.

In some embodiments, a synthetic support is tubular in shape. In specific embodiments, a synthetic support is configured to surround at least a portion of a processed trachea. In very specific embodiments, a synthetic support envelopes at least 10% of the outer surface of a processed trachea such as at least about 20%, 30%, 40%, or 50%.

A synthetic support can be defined by a length, diameter, and thickness. The term "length" as utilized herein in relation to a synthetic support is the longest distance between two ends of the synthetic support along a line that is in the same plane as and approximately parallel to the axis of the processed trachea with which the synthetic support is associated. The term "diameter" as utilized herein in relation to a synthetic support is the average diameter of the space of the synthetic support in which the processed trachea is positioned in the context of a tracheal implant, i.e., the diameter of the synthetic support is an internal diameter unless otherwise apparent by context. The term "thickness" as utilized herein in relation to a synthetic support is the thickness of the material of the synthetic support between an internal, concave surface and an external, convex surface of the synthetic support.

A synthetic support comprises a thickness. In some embodiments, the thickness is the smallest dimension of the synthetic support other than the dimensions that relate to pores within the synthetic support. In specific embodiments, the thickness of the synthetic support is less than 5 cm such as less than 4 cm, less than 3 cm, less than 2 cm, less than 1 cm, less than 9 mm, less than 8 mm, less than 7 mm, or less than 6 mm. In more specific embodiments, the synthetic support comprises a thickness of about 0.5 mm to about 1 cm. In very specific embodiments, the thickness of the synthetic support is about 100 μm to about 5 cm such as about 200 μm to about 1 cm or about 500 μm to about 5 mm.

The length of the synthetic support is subject-dependent. In some embodiments, a length of a synthetic support ranges from about 1 cm to about 15 cm such as about 2 cm to about 15 cm. In specific embodiments, the synthetic support comprises a length of about 2 cm to about 15 cm.

The internal diameter of the synthetic support is subject-dependent. In some embodiments, an internal diameter of a synthetic support ranges from about 5 mm to about 5 cm.

In very specific embodiments, the synthetic support comprises an internal diameter of about 0.5 cm to about 5 cm; a thickness of about 0.5 mm to about 1 cm; and a length of about 2 cm to about 15 cm.

In some embodiments, a synthetic support is a helix. In embodiments wherein the synthetic support is a helix, the helix can have the same or opposite handedness relative to any helix of the processed trachea. A helix of a synthetic support that has opposite handedness relative to a helix of a processed trachea can provide stability by adding structural integrity against the grain of the one or more incisions of the processed trachea. A helix of a synthetic support that has the same handedness as a helix of a processed trachea can provide stability by reinforcing a seam defined by the one or more incisions of the processed trachea.

In very specific embodiments, a synthetic support and a processed trachea of a tracheal implant comprise helices comprising the same handedness and approximately the same helix angle and helix lead such that the synthetic support reinforces the seam of a helical incision in the processed trachea.

In some embodiments, a synthetic support comprises a helix. The helix can be defined by a central axis. In specific embodiments, the helix comprises a thread that encircles the central axis. In specific embodiments, the thread comprises a bottom edge and a top edge separated by a space. In specific embodiments, the thread comprises a lead. In very specific embodiments, greater than 10% of the distance of the lead corresponds to space and less than 90% of the lead corresponds to thread. In specific embodiments, the thread comprises a biocompatible polymer of a synthetic support.

In some embodiments, a synthetic support is defined by a helix. In specific embodiments, the helix comprises a thread which is material such as biocompatible polymer. In some embodiments, the thread comprises a bottom edge and top edge. In some embodiments, the bottom edge and top edge of a thread of a helix are separated such that the helix includes space that separates the top of the thread from the bottom of the thread.

In some embodiments, a space permits direct contact between the processed trachea and cells, blood vessels, extracellular fluid, and/or extracellular matrix of a subject after the tracheal implant is implanted in a subject.

The helix can be defined by a lead. The term "lead" as utilized herein in relation to a synthetic support includes the distance between two points on the bottom edge of a thread, wherein the two points are related by both a 360° rotation of the thread about the axis and a translation in the same plane as the axis. The term "lead" as utilized herein in relation to a synthetic support includes the distance between two points on the top edge of the thread, wherein the two points are related by both a 360° rotation of the thread about the axis and a translation in the same plane as the axis. In specific embodiments, greater than 10% of the distance of the lead corresponds to space, which is not synthetic support, and less than 90% of the distance of the lead corresponds to thread, which is synthetic support. In very specific embodiments, the space is filled with fluid such as aqueous solution and/or gas.

In some embodiments, a helix comprises a lead as described herein. In specific embodiments, greater than 10% of the lead of a helix of a synthetic support is space and less than 90% of the lead of the helix is thread. In more specific embodiments, greater than 20% of the lead of a helix of a synthetic support is space and less than 80% of the lead of the helix is thread; or greater than 30% of the lead of a helix of a synthetic support is space and less than 70% of the lead of the helix is thread. In even more specific embodiments, about 20% to 67% of the lead of a helix of a synthetic support is space, and about 33% to 80% of the lead of the helix is thread. In very specific embodiments, about 33% to 67% of the lead of a helix of a synthetic support is space, and about 33% to 67% of the lead of the helix is thread.

A helix can comprise an angle as described herein. In some embodiments, a helix of a synthetic support has an angle of about 5° to about 85° relative to its axis such as about 5° to about 25°, about 15° to about 35°, about 25° to about 45°, about 35° to about 55°, about 45° to about 65°, about 55° to about 75°, about 65° to about 85°, about 5° to about 15°, about 10° to about 20°, about 15° to about 25°, about 20° to about 30°, about 25° to about 35°, about 30° to about 40°, about 35° to about 45°, about 40° to about 50°, about 45° to about 55°, about 50° to about 60°, about 55° to about 65°, about 60° to about 70°, about 65° to about 75°, about 70° to about 80°, or about 75° to about 85°.

A helix can comprise a lead as described herein. In some embodiments, a helix of a synthetic support has a lead of about 1 mm to about 8 cm such as about 1 mm to about 2 cm, about 1 cm to about 3 cm, about 2 cm to about 4 cm, about 3 cm to about 5 cm, about 4 cm to about 6 cm, about 5 cm to about 7 cm, about 6 cm to about 8 cm, about 1 mm to about 10 mm, about 5 mm to about 15 mm, about 10 mm to about 20 mm, about 15 mm to about 25 mm, about 20 mm to about 30 mm, about 25 mm to about 35 mm, about 30 mm to about 40 mm, about 35 mm to about 45 mm, about 40 mm to about 50 mm, about 45 mm to about 55 mm, about 50 mm to about 60 mm, about 55 mm to about 65 mm, about 60 mm to about 70 mm, about 65 mm to about 75 mm, or about 70 mm to about 80 mm.

In some embodiments, a synthetic support is biodegradable. In specific embodiments, a synthetic support is biodegradable upon implantation into a subject. In specific embodiments, a synthetic support comprises a biodegradable polymer. Porosity and pore size also affect biodegradability, and methods of modifying porosity and pore size to vary the rate of biodegradation in vivo are known.

In some embodiments, a synthetic support biodegrades at a rate of at least 10% per year in vivo at a temperature of about 98±1° F. or about 37±1° C. In specific embodiments, a synthetic support biodegrades at a rate of at least 20%, 25%, 30%, 33%, 40%, or 50% per year in vivo at a temperature of about 98±1° F. or about 37±1° C.

A reference biodegradation rate can be determined, for example, by incubating a solid support in phosphate buffered saline at a temperature of about 98±1° F. or about 37±1°. The in vivo biodegradation rate is typically greater than the foregoing reference biodegradation rate, for example, because a synthetic support placed in situ is subjected to (a) enzymes and other molecules that catalyze biodegradation; (b) thermodynamic sinks as the subject clears biodegradation products; and (c) the ordinary movement of a subject, which increases the rate of diffusion of both (y) molecules to the synthetic support, which increases biodegradation and (z) biodegradation products from the synthetic support, which similarly increases biodegradation.

In some embodiments, a synthetic support biodegrades at a rate of at least 10% per year ex vivo in aqueous solution at neutral pH and a temperature of about 98±1° F. or about 37±1° C. In specific embodiments, a synthetic support biodegrades at a rate of at least 20%, 25%, 30%, 33%, 40%, or 50% per year ex vivo in aqueous solution at neutral pH and a temperature of about 98±1° F. or about 37±1° C.

Biodegradation rate may be precisely tuned by varying the polymer composition of a synthetic support and/or by varying the porosity and/or pore size of the synthetic support.

In some embodiments, a tracheal implant comprises a component of an extracellular matrix. In specific embodiments, the component of an extracellular matrix is a component of an extracellular matrix that does not cause an immunogenic response in humans. In more specific embodiments, the component is a human extracellular matrix protein. In very specific embodiments, the component is a component of the human extracellular matrix that occurs at or near the trachea.

In some embodiments, a tracheal implant comprises a component of an extracellular matrix, wherein the component is a proteoglycan, polysaccharide, protein, or glycoprotein.

In some embodiments, a synthetic support comprises one or more components of the human extracellular matrix. In specific embodiments, the one or more components of the human extracellular matrix are associated with pores of the synthetic support, e.g., pores of the synthetic support may comprise the one or more components.

In some embodiments, a synthetic support comprises a coating. In specific embodiments, the coating comprises one or more components of the human extracellular matrix.

In specific embodiments, the one or more components are selected from proteoglycans (e.g., heparin sulfate, chondroitin sulfate, keratin sulfate), polysaccharides (e.g., hyaluronic acid), proteins (e.g., collagen, fibrin, elastin, laminin), and glycoproteins (e.g., fibronectin). In specific embodiments, the one or more components are tracheal extracellular matrix, e.g., protease-treated tracheal extracellular matrix.

In some embodiments, a synthetic support comprises a hormone, cytokine, or growth factor. In specific embodiments, the hormone, cytokine, or growth factor is associated with pores of the synthetic support, e.g., pores of the synthetic support may comprise the hormone, cytokine, or growth factor.

In some embodiments, the synthetic support comprises a coating, and the coating comprises a hormone, cytokine, or growth factor.

In some embodiments, the synthetic support comprises one or more pharmaceutical agents. In specific embodiments, the one or more pharmaceutical agents includes one or more immunosuppressants, antibiotics, anti-inflammatory agents (e.g., steroidal and/or nonsteroidal anti-inflammatory agents), or anticoagulants. In specific embodiments, the one or more pharmaceutical agents are associated with pores of the synthetic support, e.g., pores of the synthetic support may comprise the one or more pharmaceutical agents.

In some embodiments, the synthetic support comprises a coating, and the coating comprises the one or more pharmaceutical agents.

In some embodiments, the tracheal implant comprises stem cells. In specific embodiments, the stem cells originate from a different donor than the donor of the processed trachea. In very specific embodiments, the stem cells are associated with pores of the synthetic support, e.g., pores of the synthetic support comprise the stem cells. In some embodiments, the stem cells are associated with the processed trachea.

In some embodiments, the processed trachea is sutured, glued, or otherwise attached to the synthetic support using a biocompatible mechanical or chemical fastening agent. In some embodiments, the processed trachea is attached to the synthetic support without any fastening agent, and the processed trachea nevertheless remains in place simply by the mechanical properties of the synthetic support, e.g., including friction.

In some embodiments, a tracheal implant comprises sutures or glue, e.g., wherein the sutures or glue attach the processed trachea to the synthetic support and/or the sutures or glue configure the processed trachea in a processed configuration.

In some embodiments, a synthetic support is shaped and sized for transplantation into a subject, e.g., the synthetic support is 3D printed based on the actual shape and size of the trachea of the subject. In specific embodiments, the synthetic support is derived from imaging a trachea of a subject and 3-D printing the synthetic support based on the imaging.

In some embodiments, a tracheal implant comprises adipocytes, wherein the adipocytes are located in the lumen of the processed trachea. In specific embodiments, the adipocytes are from the planned recipient of the tracheal implant (i.e., a subject as described herein). In some embodiments, a tracheal implant comprises epithelial cells, wherein the epithelial cells are located in the lumen of the processed trachea. In specific embodiments, the epithelial cells are from the planned recipient of the tracheal implant (i.e., a subject as described herein). In some embodiments, a tracheal implant comprises tracheal cells (e.g., goblet cells), wherein the tracheal cells were obtained from a tracheal biopsy, and the tracheal cells are located in the lumen of the processed trachea. In specific embodiments, the tracheal cells (e.g., goblet cells) are from the planned recipient of the tracheal implant (i.e., a subject as described herein).

Various aspects of the disclosure relate to a method of treating a subject in need of a tracheal implant.

In some embodiments, a method of treating a subject in need of a tracheal implant comprises obtaining conformational information of a trachea and implant region of the subject; fabricating a subject-specific synthetic support based on the conformational information; providing a donor trachea; making one or more incisions in the donor trachea to yield a processed trachea; suturing the processed trachea to the synthetic support; and implanting the processed trachea and synthetic support in the subject.

In some embodiments, a method of treating a subject in need of a tracheal implant comprises implanting a tracheal implant as described herein into the subject. In some embodiments, a tracheal implant is implanted into the thorax, neck, and/or head of the subject. In some embodiments, a tracheal implant is implanted into the subject at a location that is not the thorax, neck, or head of the subject such as the abdomen of the subject.

In some embodiments, a method comprises obtaining an image of the neck of the subject. In some embodiments, a method comprises creating a subject-specific synthetic support based on the image. In some embodiments, a method comprises providing a donor trachea. In some embodiments, a method comprises making one or more incisions in the donor trachea. In some embodiments, a method comprises suturing the donor trachea to the synthetic support. In some embodiments, a method comprises implanting the donor trachea and synthetic support in the subject.

In some embodiments, a method comprises determining the size and shape of a synthetic support, wherein the size and shape of the synthetic support is determined by directly or indirectly measuring the size and shape of the neck or trachea of the subject.

In some embodiments, a method comprises creating a digital model of the existing trachea of the subject. In specific embodiments, a method comprises creating a digital model of the synthetic support based on the digital model of the existing trachea, thereby determining the size and shape of the synthetic support. In specific embodiments, obtaining conformational information comprises medical imaging. In very specific embodiments, medical imaging comprises one or more of computed tomography and magnetic resonance imaging. In very specific embodiments, a digital model is created based on computed tomography or magnetic resonance imaging data.

In some embodiments, a method comprises creating a digital model of the trachea of the subject from the conformational information; and creating a digital model of the synthetic support based on the digital model of the trachea.

In some embodiments, a method comprises fabricating a synthetic support. In specific embodiments, a synthetic support is fabricated by 3D printing.

In some embodiments, a method comprises manufacturing a synthetic support. In specific embodiments, a synthetic support is manufactured by 3D printing, e.g., such that the synthetic support is custom-tailored to fit the subject.

In some embodiments, a method comprises processing a trachea to produce the processed trachea, wherein the processing comprises making the one or more incisions in the trachea. In specific embodiments, one or more incisions define a helix in the processed trachea.

In some embodiments, one or more incisions confer a helical configuration to the processed trachea.

In some embodiments, a method comprises suturing the processed trachea to the synthetic support. In some embodiments, a method lacks the step of suturing the processed trachea to the synthetic support. In some embodiments, a method comprises gluing the processed trachea to the synthetic support.

In some embodiments, a method comprises suturing the processed trachea along a seam of the one or more incisions.

In some embodiments, suturing either increases or decreases a diameter of the processed trachea relative to its native configuration.

In some embodiments, a method comprises contacting an area of a processed trachea or synthetic support with stem cells.

In some embodiments, a method comprises culturing the tracheal implant in media, e.g., thereby expanding or differentiating stem cells.

In some embodiments, a method comprises inserting adipocytes into the lumen of the processed trachea. In specific embodiments, a method comprises obtaining adipocytes from the subject, e.g., by liposuction, and then inserting the adipocytes into the lumen of the processed trachea. In some embodiments, a method comprises inserting epithelial cells into the lumen of the processed trachea. In specific embodiments, a method comprises obtaining epithelial cells from the subject, e.g., by biopsy, and then inserting the epithelial cells into the lumen of the processed trachea. In some embodiments, a method comprises inserting tracheal cells into the lumen of the processed trachea. In specific embodiments, a method comprises obtaining tracheal cells from the subject, e.g., by biopsy, and then inserting the tracheal cells into the lumen of the processed trachea. In some embodiments, a method comprises inserting stem cells into the lumen of the processed trachea. In specific embodiments, a method comprises obtaining stem cells from the subject and then inserting the tracheal cells into the lumen of the processed trachea. Stem cells may be obtained, for example, from blood although the precise origin of the stem cells is not particularly limiting.

In very specific embodiments, a subject is human. In specific embodiments, a subject is avian, murine, lagomorpha, feline, canine, porcine, ovine, bovine, equine, or primate.

The implants and methods described herein are particularly beneficial for subjects having body size that vary from available donor trachea. In some embodiments, a subject is a human less than 18, 17, 16, 15, 14, 13, 12, 11, 10, 9, 8, 7, 6, 5, 4, 3, 2, or 1 year old. In some embodiments, a subject is a newborn human. In specific embodiments, a subject is a human who is 1 week old to 18 years old, 1 week to 16 years, 1 week to 14 years, 1 week to 12 years, 1 week to 10 years, 1 year to 18 years, 1 year to 16 years, 1 year to 14 years, 1 year to 12 years, or 1 year to 10 years. In specific embodiments, a subject has an existing trachea that is less than 90%, 80%, 70%, 60%, or 50% of the size of a full-grown adult trachea.

In some embodiments, the processed trachea is an adult trachea.

In specific embodiments, a subject is a human of less than 18, 17, 16, 15, 14, 13, 12, 11, 10, 9, 8, 7, 6, 5, 4, 3, or 2 years old, wherein the existing trachea of the subject is less than 90%, 80%, 70%, 60%, or 50% of the size of a standard adult trachea. The term "standard adult trachea" as utilized herein refers to the average trachea size in a United States tissue bank.

In very specific embodiments, a subject is a human of less than 18 years old, wherein the existing trachea of the subject is less than 90% of the size of a standard adult trachea.

In very specific embodiments, a subject is a human of less than 16 years old, wherein the existing trachea of the subject is less than 70% of the size of a standard adult trachea.

EXEMPLIFICATION

Figure 1:
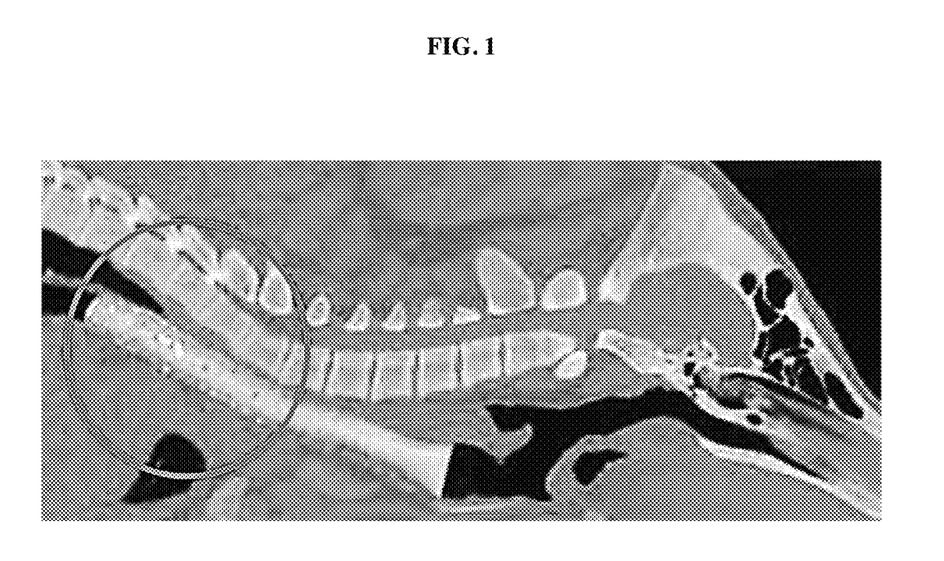
FIG. 1 is an image of a computed tomography scan of a sagittal view of a pig. The circled, cylindrically-shaped object is a volume-rendering, which defines the shape and size of a synthetic support of a tracheal implant.

Example 1. Determining the Shape and Size of a Tracheal Implant and Synthetic Support A three-dimensional image of the head, neck, and thorax of a human subject ("patient") is rendered using computed tomography or magnetic resonance imaging data. A portion of the existing trachea of the patient, which requires replacement, is rendered in three dimensions. An example of a computed tomography image of a pig is shown in FIG. 1, in which a portion of the trachea is rendered in three dimensions. A pig trachea has a similar size and shape as a human trachea.

The three-dimensional image of the trachea is used to design a synthetic support, which is rendered in three dimensions. The synthetic support has a patient-specific inner diameter and a patient-specific length. The thickness of the synthetic support is about 1 mm. The synthetic support optionally contains helical patterning that corresponds to the helical patterning of a processed trachea. In some embodiments, the helical patterning has about an 8 mm lead.

The microstructure of the synthetic support is rendered to include pores. The porosity, pore size, and pore connectivity of the synthetic support are selected based on the chemical composition of the synthetic support, its desired mechanical properties, and its desired half-life in vivo. Exemplary parameters include a porosity of 37% to 55%, compressive modulus of 52 to 68 MPa, and strength of 2.0 to 3.2 MPa in a synthetic support made from poly(caprolactone). Increased porosity at constant pore size and connectivity decreases compressive modulus, decreases strength, and increases the rate of biodegradation. Increased pore size at constant porosity and connectivity increases compressive modulus, increases strength, and decreases the rate of biodegradation. Altering pore connectivity can either increase or decrease the foregoing parameters depending upon the geometry of a network of pores. Varying a polymer from which a synthetic support is manufactured also affects compressive modulus, strength, and biodegradation.

The three-dimensional model of the synthetic support is 3D-printed using a biocompatible polymer that corresponds to the microstructure of the model. A poly(caprolactone) synthetic support can be printed using known methods, for example, with a linear print speed of 300 mm/minute at a bed temperature of 37° C. and an extrusion temperature of 70° C.

Example 2. Processing a Human Trachea

Figure 2:
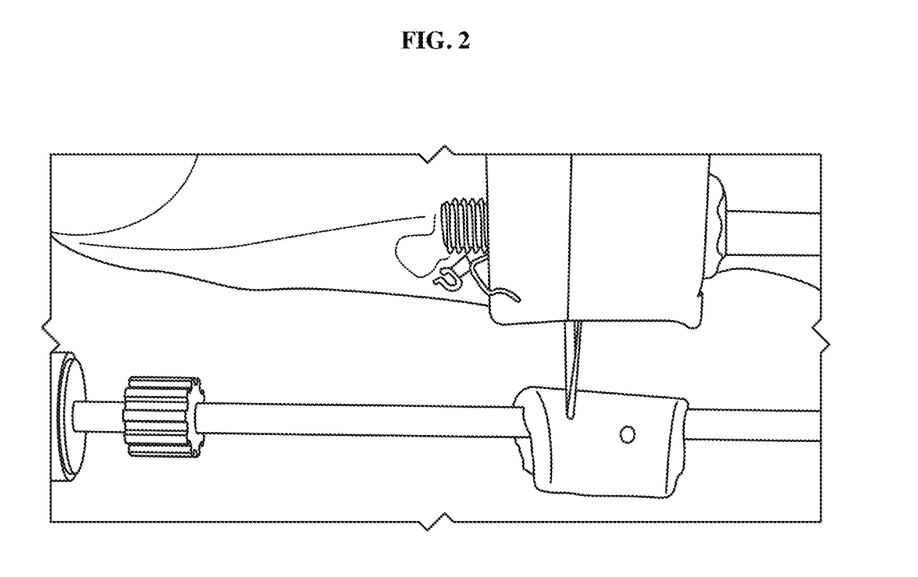
FIG. 2 is an image of a decellularized trachea and blade during a process to create a helical incision in the trachea.

An unprocessed, decellularized, human trachea is obtained from a tissue bank. A helical incision is made in the unprocessed trachea by simultaneously rotating the trachea about its axis and translating a blade along the axis at constant rates thereby producing a processed, human trachea. An image of a device used to create a helical incision in a trachea is shown in FIG. 2.

Example 3. Combining a Processed Human Trachea and a Synthetic Support

The synthetic support of Example 1 is coated with a decellularized tracheal composition. The composition is prepared by digesting decellularized extracellular matrix with pepsin. The synthetic support is submerged in the composition and then dried.

The processed, human trachea of Example 2 is overwound or underwound to fit within the synthetic support. The processed, human trachea is then sutured to the synthetic support. The incision(s) of the processed, human trachea are optionally sutured closed in the overwound or underwound configuration.

The combined sutured, processed, human trachea and synthetic support is a complete tracheal implant. The tracheal implant is then implanted into a human subject according to known methods.

Example 4. Combining a Processed Rabbit Trachea and a Synthetic Support

Figure 3:
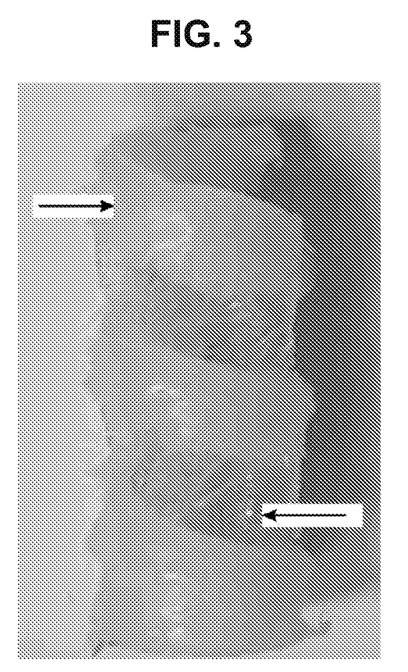
FIG. 3 is an image of a tracheal implant. The top left arrow marks the synthetic support, which is positioned on the outside of the processed trachea. The bottom right arrow marks the processed trachea.
Figure 4:
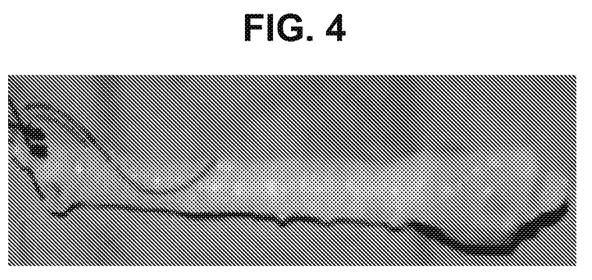
FIG. 4 is an image of a processed trachea that was sutured back together prior to implantation in a rabbit.
Figure 5:
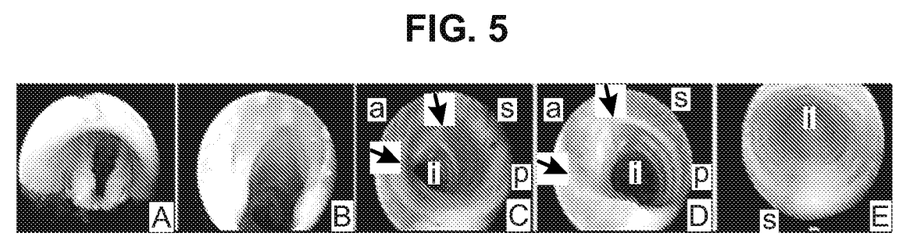

Two rabbit tracheas are obtained from rabbit donors and then decellularized. A digital model of a synthetic support is created based on the size and shape of the rabbit tracheas. A synthetic support is manufactured by 3D printing the digital model with poly(caprolactone). A helical incision is made in each rabbit trachea (unprocessed trachea) by simultaneously rotating the trachea about its axis and translating a blade along the axis at constant rates, thereby resulting in a processed trachea. An image of a device used to create helical incisions in rabbit tracheas is shown in FIG. 2. One processed trachea is sutured within the synthetic support. An image of a tracheal implant comprising a processed rabbit trachea within a synthetic support is shown in FIG. 3. One processed trachea is sutured without a synthetic support. An image of a processed rabbit trachea without a synthetic support is shown in FIG. 4.

Morselized tracheal biopsies and fat harvested by liposuction are placed within the lumen of both processed trachea. The processed trachea within the synthetic support and the processed trachea without a synthetic support are imbedded in situ in the rectus abdominis muscle of different live rabbit hosts. The trachea are allowed to heal for one month in vivo.

Figure 6:
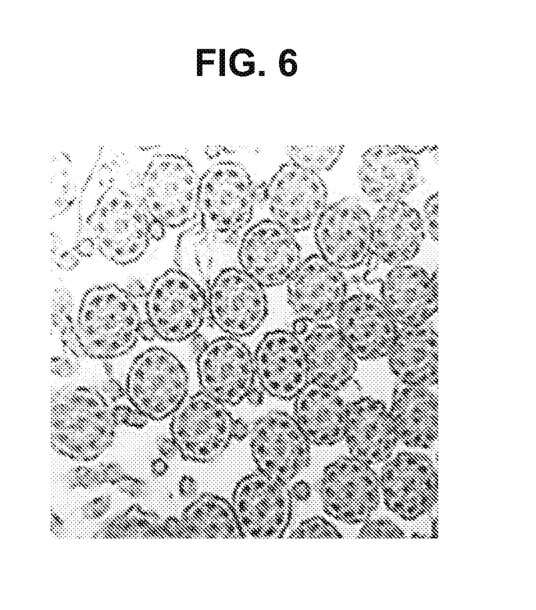
FIG. 6 is an image of the cellular morphology of a native trachea.
Figure 7:
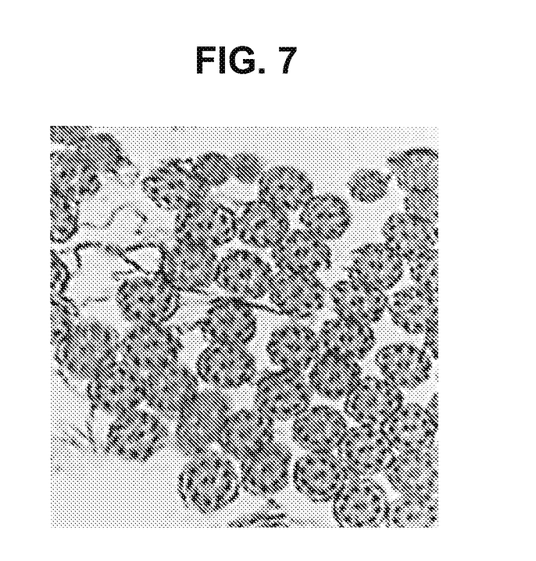
FIG. 7 is an image of the cellular morphology of cells obtained from the decellularized region of a tracheal implant after implantation into a rabbit, which is indistinguishable from the native cellular morphology shown in FIG. 6.
Figure 8:
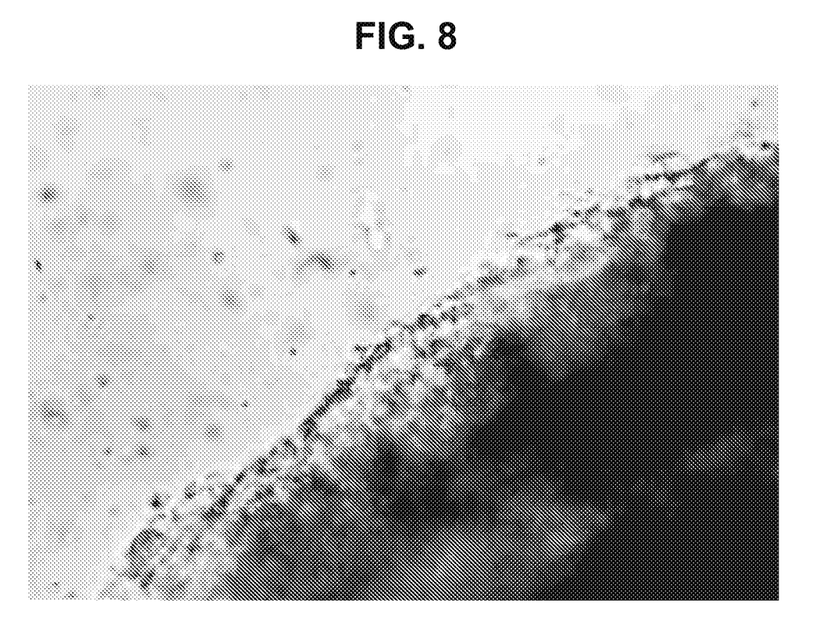
FIG. 8 is an image of the epithelial lining of a native trachea displaying cilia and mucin.
Figure 9:
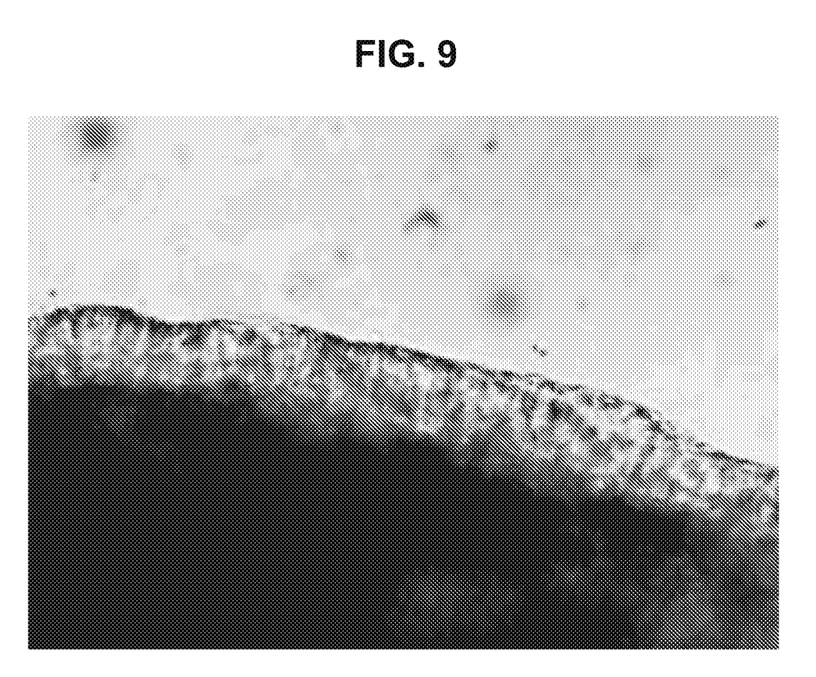
FIG. 9 is an image of the epithelial lining of the decellularized region of a tracheal implant after implantation into a rabbit, which is indistinguishable from the native epithelial lining shown in FIG. 8.

After one month, bronchoscopy of the grafts demonstrates that each decellularized, processed trachea displays native-like cells and tissue and that the sutures healed with minimal scarring. Actual images of the decellularized, processed trachea without the synthetic support are shown in FIG. 5A-5E. Microscopy of the decellularized, processed trachea demonstrates that each trachea displays native-like cells and tissue including the development of cilia and mucous within the lumen of the trachea. The cellular morphology of each tracheal implant is indistinguishable from fresh, unprocessed trachea. Actual microscopy images of fresh, unprocessed trachea are shown in FIGS. 6 & 8, and actual microscopy images of tissue obtained from decellularized, processed trachea without a synthetic support are shown in FIGS. 7 & 9.

Those skilled in the art will recognize, or be able to ascertain using no more than routine experimentation, many equivalents to the specific embodiments of the invention described herein. The scope of the present invention is not intended to be limited to the above Description and Examples, but rather is as set forth in the appended claims. It will be appreciated that the invention is in no way dependent upon particular results achieved in any specific example or with any specific embodiment. Articles such as "a", "an" and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given composition or method. The invention also includes embodiments in which more than one, or all group members are present in, employed in, or otherwise relevant to a given composition or method. Furthermore, it is to be understood that the invention encompasses all variations, combinations, and permutations in which one or more limitations, elements, clauses, descriptive terms, etc., from one or more of the listed claims or from the description above is introduced into another claim. For example, any claim that is dependent on another claim can be modified to include one or more elements, limitations, clauses, or descriptive terms, found in any other claim that is dependent on the same base claim. Furthermore, where the claims recite a composition, it is to be understood that methods of using the composition for any of the purposes disclosed herein are included within the scope of the invention, and methods of making the composition according to any of the methods of making disclosed herein are included within the scope of the invention, unless otherwise indicated or unless it would be evident to one of ordinary skill in the art that a contradiction or inconsistency would arise. It should also be understood that, in general, where the invention, or embodiments and aspects of the invention, is/are referred to as comprising particular elements, features, etc., certain embodiments of the invention or aspects of the invention consist, or consist essentially of, such elements, features, etc. "Consist essentially" in accordance with the disclosure means that in addition to the recited element(s), non-essential elements may or may not be present.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise. Any particular embodiment, aspect, element, feature, etc., of the present invention, or any combination thereof, may be explicitly excluded from any one or more claims whether or not such exclusion is expressly recited herein.

The invention claimed is:

1. A tracheal implant, comprising: a trachea processed to comprise one or more incisions providing a helical configuration to the processed trachea, wherein the processed trachea comprises a single, continuous tissue; and a subject-specific synthetic support.

2. The tracheal implant according to claim 1, the processed trachea comprising a lumen comprising a diameter, wherein the diameter varies from a diameter prior to processing.

3. The tracheal implant of claim 2, wherein the diameter varies from the diameter prior to processing by 200 µm to 2 cm.

4. The tracheal implant of claim 1, wherein the processed trachea comprises decellularized tissue.

5. The tracheal implant of claim 1, wherein the processed trachea comprises a human trachea.

6. The tracheal implant of claim 1, wherein the synthetic support comprises a biocompatible polymer.

7. The tracheal implant of claim 6, wherein the biocompatible polymer comprises one or more of poly(caprolactone) (PCL), poly(vinyl acetate) (PVAC), ethylene vinyl acetate polymer (EVA), polyvinyl alcohol (PVA), poly(lactic acid) (PLA), poly(glycolic acid) (PGA), poly(lactic-co-glycolic acid) (PLGA), polyalkyl cyanoacrylate, polyurethane, nylons, stereoisomers of the foregoing, and copolymers of two or more of the foregoing.

8. The tracheal implant of claim 7, wherein the biocompatible polymer comprises poly(caprolactone).

9. The tracheal implant of claim 1, wherein the synthetic support comprises a porosity of 5% to 90%.

10. The tracheal implant of claim 9, wherein:
the synthetic support comprises a network of pores comprising openings on the surface of the synthetic support; and
the openings are in fluid communication with the network of pores.

11. The tracheal implant of claim 10, wherein: the openings have an average surface area of 1000 $m^2$ to 100 $mm^2$ per opening; and greater than 50% of the openings on the surface of the synthetic support are in fluid communication with at least 4 other openings on the surface of the synthetic support such that fluid may enter an opening on the surface of the synthetic support and exit the synthetic support through any one of the at least 4 other openings.

12. The tracheal implant of claim 1, wherein the synthetic support comprises a compressive modulus of 20 MPa to 200 MPa.

13. The tracheal implant of claim 1, wherein the synthetic support comprises a tensile strength of 1 MPa to 10 MPa.

14. The tracheal implant of claim 1, wherein the synthetic support comprises: an internal diameter of 0.5 cm to 5 cm; a thickness of 0.5 mm to 1 cm; and a length of 2 cm to 15 cm.

15. The tracheal implant of claim 1, wherein the synthetic support comprises: a helix comprising a thread encircling a central axis, the thread comprising a bottom edge and a top edge separated by a space; and a lead, wherein greater than 10% of the distance of the lead corresponds to space; and less than 90% of the distance of the lead corresponds to thread.

16. The tracheal implant of claim 1, wherein the synthetic support is biodegradable.

17. The tracheal implant of claim 1, wherein the synthetic support comprises a coating comprising at least one component of a human extracellular matrix.

18. The tracheal implant of claim 17, wherein the component of the human extracellular matrix comprises a proteoglycan, polysaccharide, protein, or glycoprotein.

19. The tracheal implant of claim 17, wherein with the coating comprises tracheal extracellular matrix.

20. The tracheal implant of claim 1, wherein the processed trachea is sutured to the synthetic support.

21. The tracheal implant according to claim 1, wherein a conformation of the synthetic support is derived from imaging a subject's trachea and 3-D printing the synthetic support based on the imaging such that the synthetic support is subject-specific.

22. The tracheal implant of claim 1, further comprising stem cells, wherein the stem cells originate from a donor different than a donor of the processed trachea.

23. A method of treating a subject in need of a tracheal implant, comprising implanting the tracheal implant of claim 1 into the subject.

* * * * *